United States Patent [19]

Wallace

[11] Patent Number: 4,610,256
[45] Date of Patent: Sep. 9, 1986

[54] PRESSURE TRANSDUCER

[75] Inventor: William D. Wallace, Salt Lake City, Utah

[73] Assignee: Utah Medical Products, Inc., Midvale, Utah

[21] Appl. No.: 654,373

[22] Filed: Sep. 25, 1984

[51] Int. Cl.⁴ .............................................. A61B 5/02
[52] U.S. Cl. .................................. 128/675; 128/673; 73/706; 73/721; 73/740; 73/4 R
[58] Field of Search ................................ 128/672–673, 128/675, 748; 73/715, 721, 706, 708, 740, 4 R

[56] References Cited

U.S. PATENT DOCUMENTS

| | | | |
|---|---|---|---|
| 3,803,917 | 4/1974 | Reese et al. | 73/708 |
| 4,072,056 | 2/1978 | Lee | 128/675 X |
| 4,185,641 | 1/1980 | Minior et al. | 128/675 |
| 4,226,124 | 10/1980 | Kersten | 128/675 X |
| 4,237,900 | 12/1980 | Schulman et al. | 128/673 X |
| 4,252,126 | 2/1981 | Mandl | 128/675 X |
| 4,282,881 | 8/1981 | Todd et al. | 128/675 X |
| 4,342,218 | 8/1982 | Fox | 128/673 X |
| 4,365,635 | 12/1982 | Bowman | 128/675 |
| 4,407,296 | 10/1983 | Anderson | 128/675 |
| 4,539,998 | 9/1985 | McCord et al. | 128/675 |

OTHER PUBLICATIONS

Advertisement, Bruton Industries B200 Dynamic Blood Pressure Calibrator/Tester/Execiser (Feb. 1984).
J. M. R. Bruner, "Handbook of Blood Pressure Monitoring," pp. 115–120 (1978).
Advertisement, Bio-Tek Instruments, Inc., Pneumatic Transducer Tester Model DPM-1.
Nursing Photo Book: "Using Monitors" pp.20–47, 72–79.

Primary Examiner—Kyle L. Howell
Assistant Examiner—Angela D. Sykes
Attorney, Agent, or Firm—Workman, Nydegger & Jensen

[57] ABSTRACT

A pressure transducer which includes a novel apparatus and method for calibrating a pressure transducer to a monitor used in connection with an indwelling catheter to monitor a patient's blood pressure. The pressure transducer includes a transducer diaphragm disposed within a housing cavity. A manometer and a syringe are connected so as to be in communication with the transducer cavity. By partially withdrawing the plunger of the syringe, the pressure in the transducer cavity is reduced, thereby establishing a pressure drop equal to that measured by the manometer across the transducer diaphragm, thus facilitating calibration of the pressure measurement system. Inasmuch as the indwelling catheter is isolated from the pressure calibration apparatus, the methods and apparatus of the present invention avoid any risk of introducing air bubbles or microorganisms into the indwelling catheter.

42 Claims, 10 Drawing Figures

PRESSURE TRANSDUCER

BACKGROUND

1. The Field of the Invention

The present invention relates to pressure transducers for medical use. More particularly, the present invention is directed to a novel pressure transducer for use in direct measurement of human blood pressure, and which includes a novel apparatus and method for calibrating the transducer.

2. The Prior Art

Perhaps the most frequently measured condition of a patient undergoing evaluation, diagnosis, or treatment is the patient's blood pressure. For example, blood pressure measurement and monitoring are regularly employed with patients suffering from shock or caridovascular ailments. Advantageously, by monitoring the blood pressure of these and other types of patients, medical personnel are better able to detect blood flow difficulties and other cardiovascular problems at an early stage. As a result, the use of blood pressure measurement and continuous monitoring may increase the likelihood that a patient can be successfully diagnosed and treated with needed emergency assistance.

A variety of methods are currently used for measuring and/or monitoring blood pressure. For example, medical personnel frequently use various indirect blood pressure measurement techniques, such as measuring a patient's blood pressure by using a pressure cuff and a stethoscope. Blood pressure measurements can also be made by using invasive techniques which permit direct measuring and monitoring of blood pressure. Notably, when diagnosing and treating critically ill patients, direct blood pressure measurements are greatly preferred over indirect measurements.

This preference for direct blood pressure measurement is due to several factors. First, the use of direct blood pressure measurement greatly increases the accuracy of the blood pressure reading. Typical indirect techniques may, for example, yield errors as high as ten percent, whereas direct blood pressure measurement techniques are generally accurate to within about one percent. In addition, direct monitoring techniques facilitate the continuous monitoring of a patient's blood pressure on a beat-to-beat basis. Direct blood pressure monitoring also enables the rapid detection of a change in cardiovascular activity, and this may be of significant importance in emergency situations. Further, direct blood pressure monitoring techniques can be readily used to measure and monitor a patient's blood pressure at a specific internal location, such as within the chambers of the heart. Because of these and other advantages, therefore, direct blood pressure measurement and monitoring has become a routine procedure for many critically ill patients.

One of the most widely used techniques for direct blood pressure measurement and monitoring is called catheterization. In using this technique, a needle is first inserted into a peripheral blood vessel. For example, if it is desired to monitor arterial blood pressure, the needle may be inserted into the radial artery. If, on the other hand, venous blood pressure is to be monitored, the needle may be inserted into the antecubital, radial, jugular, or subclavian veins.

Once the needle is properly inserted, a special catheter is threaded through the needle and into the blood vessel. The catheter is filled with a sterile solution, such as a sterile saline solution. In addition, the catheter may be formed so as to facilitate the further threading of the catheter along the blood vessel. Thus, the catheter may be threaded through the needle and along the blood vessel until the tip of the catheter, which is located inside the blood vessel, is positioned at the particular point within the body at which it is desired to make the blood pressure measurement. Then, with the catheter thus in place, the needle may be withdrawn.

Prior to positioning the proximal end of the indwelling catheter within a patient as described above, the distal end of the catheter is connected to pressure tubing that is connected to a pressure transducer. The catheter is generally also connected to a suitable continuous flush device or heparin drip to help prevent clotting around the tip of the catheter. The pressure transducer is also electrically connected to some type of monitor device near the patient's bedside. Typical monitor devices include cathode-ray tube display devices, digital display and/or recording devices, printers, and plotters.

In addition to the proper set-up of the measurement equipment in the above-described manner, it is also highly important to prime the catheter and tubing with the sterile solution so that any air bubbles within the catheter and tubing are removed such that a continuous fluid column is provided from the pressure transducer to the tip of the catheter. Then, when the catheter is positioned within the patient's blood vessel, as the patient's heart thereafter pumps blood, periodic pressure pulses are transmitted through the patient's blood vessle and along the fluid column in the catheter to the pressure transducer. The pressure transducer generates electrical signals representing the pressure pulses, and such signals are then amplified and displayed by the monitor device. Usually, the monitor device is used to display the patient's blood pressure as a function of time, this type of display being commonly referred to as the blood pressure waveform. The patient's blood pressure waveform can then be used by medical personnel to appropriately diagnose and treat the patient.

It will be readily appreciated that one of the most important components of the above-described blood pressure monitoring system is the pressure transducer. Significantly, the accuracy and the precision of the pressure transducer set an upper limit to the quality of the blood pressure data which can be obtained. Therefore, those skilled in the art of blood pressure monitoring have attempted to develop pressure transducers which have a high degree of reliability, sensitivity, and accuracy.

A typical pressure transducer for use in blood pressure monitoring systems comprises a thin diaphragm which is capable of being deflected by the pressure pulses which travel through the fluid column in the catheter and tubing. Some type of mechanism is also provided for measuring the deflection of the diaphragm, usually comprising suitable electronic circuitry which is configured so as to generate an electrical signal representing the pressure exerted on the diaphragm.

While a variety of electronic mechanisms have been used to measure the deflection of a diaphragm in pressure transducers, perhaps the most common measuring mechanism which is currently in use comprises a resistive strain gauge, such a mechanism being quite similar to strain gauges that are commonly used in industrial applications. Basically, a resistive strain gauge comprises a thin resistive wire which is connected to the pressure diaphragm such that the wire is stretched whenever the diaphragm is deflected. In accordance with well-known principles, such a stretching of the wire causes the electrical resistance of the wire to increase. Assuming, therefore, that a constant voltage is being applied across the wire, such an increase in the wire's resistance will result in a corresponding decrease in the electrical current through the wire in accordance with Ohm's law. Thus, by continuously measuring the current through the wire, it is possible to obtain an electrical signal which represents the amount by which the diaphragm is being deflected and which, therefore, also represents the pressure being exerted on the diaphragm.

In order to increase the sensitivity and accuracy of the pressure measurement, it is common to connect four such resistive wires to a single pressure diaphragm. Typically, the wires are also connected together in a conventional Wheatstone bridge configuration. Moreover, two of the wires are connected to the diaphragm so as to be stretched when the diaphragm is deflected, while the other two wires are compressed as the diaphragm is deflected. A more recent technology involves state of the art integrated circuitry. By special processing the above-mentioned diaphragm can be made out of silicon with resistive material (such as Boron) diffused into the silicon in the form of a Wheatstone bridge. This makes the transducer more rugged, less expensive, and a more stable device. Significantly, using this type of diaphragm/circuitry configuration, it is possible to obtain quite precise measurements of even small pressure pulses acting on the pressure diaphragm.

Before a pressure transducer such as that described above can be used, however, it must be balanced and calibrated with the monitor to ensure that the readings it produces are accurate.

A transducer is balanced in order to establish atmospheric pressure as the baseline or zero point from which the patient's pressure is read. A transducer is often used with a disposable dome that fits over the transducer diaphragm. The dome has two ports, one on the side and one vertical. The side port is connected to the indwelling patient catheter after it is primed with saline solution. The other port is generally used for balancing and calibration.

In order to balance the transducer, the vertical port is opened to the atmosphere and the other port is shut off from the patient. The transducer is then raised or lowered until the top of the vertical port is level with the position of the indwelling tip of the catheter. For each inch off the proper level, there will be an error in the pressure reading of about 2 millimeters of mercury. The monitor is then zeroed and the transducer port recapped.

After the transducer has been balanced, it is often necessary to calibrate the system to compensate for electrical inaccuracies in the transducer (often termed the "cal factor"). With prolonged use, transducers lose some sensitivity and become less accurate, thus making it necessary to calibrate the monitor to the transducer so that the monitor will be appropriately adjusted to compensate for such inaccuracy.

The most reliable method of calibrating a pressure monitor to a transducer involves the use of a common mercury sphygmomanometer from which the pressure cuff has been removed. The rubber tubing leading to the mercury column on the sphygmomanometer is secured to one arm of a Y-connector, and the bulb that is otherwise used to inflate the pressure cuff is connected to the other arm of the Y-connector. Finally, the foot of the Y-connector is connected to the vertical port of the disposable transducer dome.

After closing off a stopcock disposed between the transducer and the patient, the sphygmomanometer bulb is pumped until the mercury column indicates an appropriate calibration pressure, such as 100 mm Hg. Because of the Y-connector, the transducer diaphragm is also subjected to the same pressure. Most likely the monitor will indicate some pressure differing from that measured by the sphygmomanometer due to inaccuracy of the transducer. The monitor's sensitivity control should be adjusted until it gives a pressure reading identical to that of the mercury column, thereby calibrating the pressure monitor to the pressure sensed at the transducer so that it gives an accurate reading. This procedure may be repeated over a range of pressures to check linearity. The sphymomanometer is then removed, the vertical port of the disposable dome is capped, and the stopcock between the transducer and the patient is opened to permit the monitoring of the patient's blood pressure.

Although effective, the use of a mercury sphygmomanometer to calibrate a pressure monitoring system in the manner described above suffers from several disadvantages. For example, the need to interconnect the sphygmomanometer to the transducer apparatus followed by pumping of air into the system to increase the pressure gives rise to a substantial risk of introducing bacteria or other microorganisms into the transducer unless the entire calibration apparatus is sterilized. Such microorganisms may then be carried into the patient through the indwelling catheter. The possibility of infection carried through an indwelling catheter is of serious concern with respect to any patient; in a seriously ill patient such as is usually the case when using direct pressure monitoring, an infection introduced through an indwelling catheter may be life-threatening.

Another disadvantage of the use of a sphygmomanometer in calibrating a transducer in the manner described above is the introduction of a liquid-air interface at the position where the liquid column in the transducer apparatus comes in contact with the air column from the sphygmomanometer. If the level of liquid in the transducer is too low, or if the technician forgets to close off the indwelling catheter, air bubbles may be introduced into the patient line as the sphygmomanometer is pumped. Even a very small amount of air introduced into the patient's bloodstream could lead to formation of an air embolism which may seriously threaten the patient's health. Further, air bubbles that are introduced into the indwelling catheter, even if not introduced into the patient, are extremely disadvantageous because they are compliant and thus dampen the blood pressure pulses, thereby reducing the ability of the monitoring system to accurately record the patient's blood pressure.

Other techniques have also been devised in the prior art to ensure that the monitor's reading corresponds to the transducer's sensitivity. Such techniques include electronic calibration procedures wherein by depressing a shunt switch on the monitor a predetermined resistance which is provided in the circuitry of the monitor or cable/connector may be shunted across the transducer output. The disadvantage of this particular technique is that it does not test the accuracy of the transducer diaphragm itself. See, Bruner, John M. R.,

*Handbook of Blood Pressure Monitoring*, pp. 115–117 (1978). Thus, when using this calibration technique one must still periodically use a mercury sphygmomanometer to apply a known pressure to the transducer diaphragm so that the monitor can then be calibrated to that pressure. Accordingly, the above-described technique does not remove the difficulties inherent in maintaining sterility and in avoiding introduction of air into the patient line.

Still another approach that has been used in the prior art is a volumetric technique such as provided with a device having a known volume which can be coupled to the pressure monitoring system. An example of this approach is exemplified by the Bruton Industries B200 dynamic blood pressure calibrator. The device works well for purposes of placing a known pressure on the transducer in order to accurately determine the necessary calibration adjustment. However, various problems remain, such as maintaining sterility as well as the fact that the volumetric device must be adjusted for different altitudes. Also, typically volumetric calibration devices are relatively expensive and somewhat complicated in their construction and use.

Another relatively recent innovation which has been made in the state of the art of direct blood pressure monitoring systems in the use of disposable pressure transducers. Previously, pressure transducers which have been used in the state of the art were quite expensive and were used many times. In order to prevent contamination when using a transducer on a new patient, disposable domes were provided for the transducer so that only the plastic dome which is screwed onto the top of the transducer is required to be discarded before reusing the transducer with another patient. However, as mentioned above, after prolonged use the sensitivity and stability of the transducer may be adversely affected and it therefore may become necessary to more frequently calibrate the transducer.

As noted above, recent advances in electronic technology have made it possible to develop small, relatively inexpensive silicon chip transducers which are completely disposable after a single use. Nevertheless, even though the cost of such disposable transducers has been greatly reduced, typically the cost is still high enough that it would be advantageous to be able to reuse such transducers at least to a limited extent, thereby providing the potential for further cost savings. To date, it has not been possible to reuse such silicon chip transducers since they are interfaced directly to the fluid-filled indwelling catheter and therefore are contaminated once they have been used.

In view of the present state of the art, it will be appreciated that it would be a significant advance in the field of direct blood pressure monitoring if methods and apparatus could be provided for calibrating pressure transducers in a manner that would not expose the patient to the risk of infection, and in a manner that would prevent the risk of introducing air bubbles into the system. It would be a further significant advantage if a pressure transducer which is small and economical enough to be disposable could be adapted for reuse to a limited extent so as to further reduce the costs involved. Such methods and apparatus are disclosed and claimed herein.

PRINCIPAL OBJECTS AND BRIEF SUMMARY OF THE INVENTION

In view of the foregoing problems experienced with conventional techniques for calibrating a pressure transducer, it is a primary object of the present invention to provide a novel means for safely and conveniently calibrating a transducer without having to sterilize the calibration system and without creating the risk of an air embolism or infection, or introducing air bubbles into the system.

It is another principal object of the present invention to provide an improved system and method for calibrating a medical pressure transducer that is simple, yet safe and effective.

Another primary object is to provide a transducer apparatus that can be easily calibrated, and that is economical enough to be disposable yet adapted for use more than a single time if desired.

These and other objects and features of the present invention will become more fully apparent from the following description and appended claims taken in conjunction with the accompanying drawings.

In accordance with the foregoing principal objects, a preferred embodiment of the transducer apparatus of the invention includes a miniature silicon chip transducer contained in a housing that can be secured to a disposable dome or to a disposable length of tubing. The transducer is vented to atmospheric pressure through the housing and an electrical cable that is attached to the housing. The electrical cable has a unique plug and socket which permit an apparatus to be attached to the cable so that a vacuum can be imposed on the backside of the transducer diaphragm, thereby facilitating calibration of the pressure monitoring system. Since the pressure transducer is a true differential device, a vacuum on the backside of the diaphragm is completely equivalent to a pressure on the patient side of the transducer. Inasmuch as all pressure adjustments are made at a point in the pressure monitoring system that is completely isolated from the patient line, there is no risk of introducing air or microorganisms into the indwelling catheter and patient line. The transducer apparatus can be economically disposed of, but is also adaptable for re-use if desired.

BRIEF DESCRIPTION OF THE DRAWINGS

In the accompanying drawings, which represent the best mode presently contemplated for carrying out the invention.

DETAILED DESCRIPTION OF THE PRESENTLY PREFERRED EMBODIMENT

The present invention can best be understood by reference to the drawings, in which like parts are designated with like numerals throughout.

Figure 1:
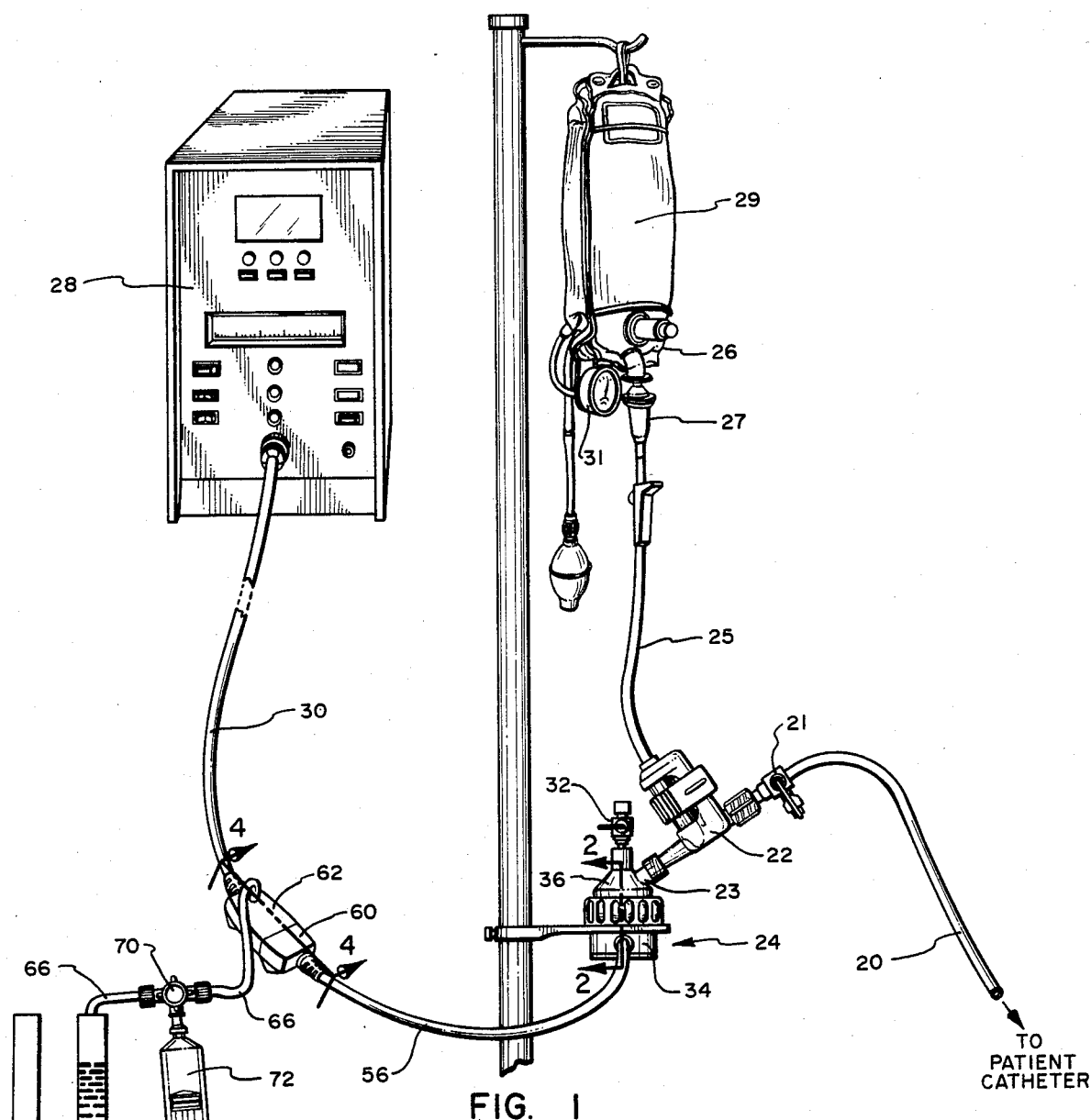
FIG. 1 is a perspective view of a pressure monitor system incorporating a presently preferred embodiment of the apparatus and method of the present invention.

Reference is first made to FIG. 1, which illustrates the incorporation of a preferred embodiment of the apparatus of the present invention into a typical pressure monitoring system. Thus, as illustrated in FIG. 1, pressure tubing 20 is adapted for connection to an indwelling catheter (not shown) inserted into a suitable body location in a patient (not shown) so as to continuously monitor variations in blood pressure at that location.

As noted above, it is useful to continuously infuse a suitable solution, such as sterile saline, through the pressure tubing 20 and indwelling catheter in order to prevent thrombus formation at the indwelling tip of the catheter. Accordingly, a continuous flush device 22 is placed between the patient and the pressure transducer apparatus 24 to permit coupling through tubing 25 to a drip chamber 27 connected at the bottom of a pressurized bag 26 of saline solution. The continuous flush device also typically maintains a slow, continuous infusion of saline for purposes of maintaining catheter patency, and also permits periodic fast flushing of saline when needed to test dynamic response of the system or to clear the line. The bag 26 is pressurized by means of a standard pressure cuff 29 which surrounds the bag 26. The cuff 29 is typically maintained at a pressure of about 300 mm Hg, and includes a suitable gauge 31 for indicating the pressure.

In setting up the pressure monitoring system, it is extremely important that all air bubbles be removed from the patient line 20, the dome 36 of transducer apparatus 24, and the various fittings such as 21, 22 and 32 to ensure that there is a completely fluid-filled column capable of accurately transmitting pressure variations to the transducer diaphragm disposed within the transducer apparatus, and to prevent any introduction of air into the patient's arterial system. As described above, deflection of the transducer diaphragm is converted to an electrical signal input to monitor 28 by means of electrical cables 56 and 30. Monitor 28 is generally adapted to provide visual real-time pressure readings so that the patient's condition may be continuously monitored.

Figure 2:
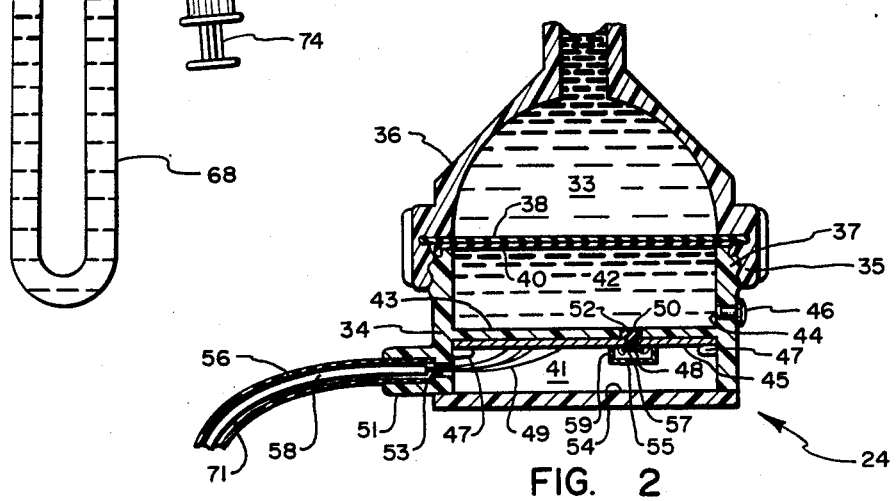
FIG. 2 is a vertical section of the pressure transducer apparatus taken along line 2—2 of FIG. 1 and drawn to a larger scale.

FIG. 2 illustrates in greater detail one presently preferred embodiment of the transducer apparatus 24. The transducer apparatus 24 is adapted to be reused a number of times, with transducer dome 36 being used once and then discarded.

The disposable dome 36 is provided with a dome diaphragm 38 which seals the opening of dome 36. Thus, a fluid-filled chamber 33 is formed which communicates through the side port 23 (see FIG. 1) with flushing device 22 and patient line 20. Dome 36 also has a threaded fitting 35 so that dome 36 can be easily attached to transducer apparatus 24 and then later removed when the dome 36 is to be discarded.

The transducer apparatus generally designated at 24 includes a plastic housing 34 which has a corresponding threaded fitting 37 at the upper end thereof. Housing 34 is generally cylindrical and is sealed at the upper end by a flexible diaphragm 40.

The dome 36 and transducer apparatus 24 are adapted to fit together such that dome diaphragm 38 and diaphragm 40 are contiguous. As a result, pressure variations transmitted through the fluid-filled indwelling catheter will be transmitted to fluid-filled chamber 33 and dome diaphragm 38, which will in turn be mechanically transmitted to diaphragm 40. The use of dome 36 with diaphragm 38 prevents leakage of solution at the threaded fittings 35 and 37, and also isolates the infusion fluid from diaphragm 40 so that transducer apparatus 24 is not contaminated at all by the infusion fluid, thus permitting only the contaminated dome 36 to be discarded after use.

The diaphragm 40 is advantageously disposed over a cavity 42 that is filled with a suitable liquid such as silicon oil which may be introduced through a port 44 and then capped by a plug 46. As a result, deflection of diaphragm 40 will be transmitted through the fluid-filled cavity 42 to transducer diaphragm 48, as hereinafter more fully explained.

With continued reference to FIG. 2, it will be seen that partition 43 which is formed as an integral part of the housing 34 divides the interior of housing 34 into the upper fluid-filled cavity 42 and a lower cavity 41 which, as hereinafter more fully explained, contains the electrical components which are used to transform the mechanical pressure pulses into corresponding electrical signals that are then input to the monitor 28. In particular, the arrangement for providing the electrical circuitry is essentially the same as the arrangement which is described in my copending U.S. application Ser. No. 608,761 filed May 9, 1984, which is incorporated herein by reference.

The lower cavity 41 which houses the electrical components includes a dielectric substrate 45 which is formed, for example, from ceramic material. Dielectric substrate 45 is in turn secured within housing 34 by means of suitable stakes 47 which may be flattened after the substrate 45 is in place by means of sonic welding so as to secure the substrate 41 within housing 34. The dielectric substrate 45 is also provided with conventional temperature compensation circuitry (not shown) which may be formed on the substrate 45 by screening or other appropriate processes, and which is attached to wires 49 carried by cable 56. Cable 56 is anchored to the bottom portion of housing 34 through a port 51 which provides access for wires 49 through an opening 53 into the lower cavity 41.

As more fully explained in the aforementioned patent application incorporated herein by reference, the temperature compensation circuit (not shown) formed on substrate 45 is used to adjust both the zero pressure point and the gain of the transducer so that these parameters will not change with variations in temperature. The temperature compensation circuit also determines the gain or sensitivity of the transducer, such gain being typically on the order of approximately five microvolts per volt of excitation per mm Hg of pressure. The temperature compensation circuit is also used to match the input and output impedance of the transducer with that of the monitor 28, typical impedances being on the order of about 350 Ohms.

Also enclosed within the lower cavity 41 of housing 34 is a small opaque cap 55 which is placed over the semiconductor transducer diaphragm 48 for mechanical protection and light isolation. Semiconductor transducer diaphragm 48 comprises a piezoresistive diaphragm and measuring circuitry consisting of four resistive elements that are ion-implanted on the diaphragm so as to form a Wheatstone bridge. The central portion of the silicon chip is etched away so as to form the thin diaphragm 48 which is then fluid-coupled to the chamber 42 by means of a silicon gel or silicon oil 52 which fills corresponding holes 50 and 57 formed through the partition 43 and dielectric substrate 45, respectively. Thus, as the piezoresistive diaphragm is deflected the resistive elements that form the Wheatstone bridge will generate corresponding electrical signals that are then input through the temperature compensation circuit and attached wires 49 to monitor 28.

The above-described arrangement for the transducer apparatus 24 is particularly advantageous. The described arrangement permits all of the electronic components, including the silicon transducer chip which forms the diaphragm 48, the temperature compensation circuit and connecting wires 49 all to be completely formed on the same side of the substrate 45, which is electrically isolated from the patient by means of the nowill conductive dielectric substances 42 and 52 and the diaphragms 40 and 38. The transducer apparatus is also completely isolated from contamination from the infusion fluid through the use of the disposable dome 36. Thus, even though the semiconductor transducer element which forms the transducer diaphragm 48 is miniaturized and is economical enough to be disposed of after each use, the above arrangement advantageously permits reuse when such is desired since only the disposable dome portion 36 need be discarded since that is the only portion which comes into contact with the infusion fluid that is in contact with the patient's bloodstream.

Cap 55 which is placed over the transducer diaphragm 48 is constructed of an opaque material, as mentioned above, in order to screen out any ultraviolet light which might adversely affect the operational characteristics of the semiconductive transducer chip. However, as explained in the background portion of the specification, the patient's pressure readings are referenced to atmospheric pressure as the baseline or zero point. Accordingly, a small hole 59 is provided through the side of cap 55 so that the transducer diaphragm 48 is vented through the cap 55 to the cavity 41. Cavity 41 is in turn vented through cable 56 to atmospheric pressure in the manner described below.

With reference again to FIG. 1, it will be seen that cable 56 terminates at an electrical plug 60 which is designed to be received in mating relationship by corresponding electrical socket 62 attached at the end of cable 30 which runs back to the monitor 28. As shown best in FIGS. 3 and 4, plug 60 has a male fitting 61 which is designed to be inserted into a corresponding female fitting 63 of socket 62 such that the metal pins 65 will be received in electrical contact in corresponding holes 67. A key 73 is formed on plug 60 and a corresponding keyway 75 is formed in socket 62 to prevent the plug 60 from being reversed when plugged into socket 62.

Figure 3:
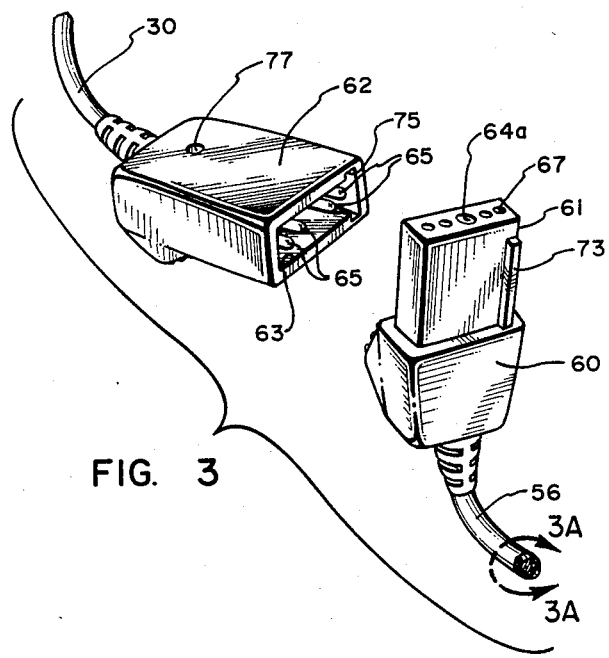
FIG. 3 is a perspective view of a presently preferred embodiment of the electrical plug and socket used for interconnecting a monitor to the transducer apparatus in accordance with the calibration method of the present invention.
Figure 3A:
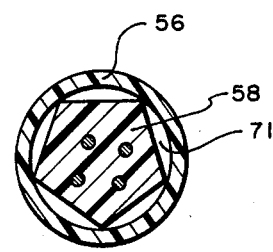
FIG. 3A is an enlarged cross-sectional view of a presently preferred embodiment of cable used for connecting the monitor and transducer apparatus, said section being taken along line 3A—3A of FIG. 3.
Figure 4:
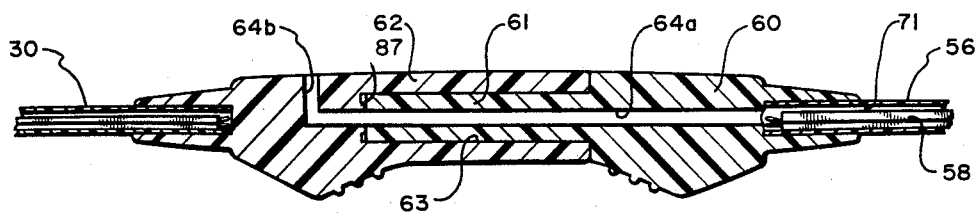
FIG. 4 is a longitudinal section of the plug and socket illustrated in FIG. 3 in coupled position, taken along line 4—4 of FIG. 1.

As shown in FIG. 4, there is a channel 64a which runs through plug 60 and which communicates with the space 71 (see, also FIG. 3A) of cable 56. Also, the socket 62 is similarly provided with a channel 64b which communicates with channel 64a and which terminates at a small hole 77 on the side of socket 62 as illustrated in FIG. 3. Channels 64b and 64a cooperate with the space 71 (see FIG. 3A) provided through the interior of cable 56 to provide a vent which communicates with atmospheric pressure. Thus, the transducer diaphragm 48 will be vented through the cap 55, cavity 41, space 71 of cable 56 and channels 64 to atmosphere.

As described above, in the past monitor/transducer calibration and verification has been achieved by connecting a sphygmomanometer to the vertical port 32 (see FIG. 1) of dome 36 while stopcock 21 is turned off to the transducer. Air has been pumped into the sphygmomanometer line until the sphygmomanometer reads a suitable pressure (typically 100 mm Hg) which is used to calibrate the transducer. The pressure exerted by the sphygmomanometer on the fluid contained in chamber 33 (see FIG. 2) of dome 36 causes the transducer diaphragm to deflect thereby generating a corresponding electrical signal measured by monitor 28. If the reading on monitor 28 is not identical to the reading on the sphygmomanometer, the monitor is then adjusted until it reads the same pressure as indicated at the sphygmomanometer.

Although this procedure is accurate, it subjects the patient to the risk of infection introduced through the sphygmomanometer tubing unless such tubing has been carefully sterilized. This of course is time consuming and adds additional expense and inconvenience each time the transducer is calibrated in this manner. This procedure also creates a risk of introducing air into the patient tubing 20 which may reduce the sensitivity of the system if an air bubble is entrapped in the patient line 20, as well as exposing the patient to the risk of an embolism if the air bubble enters the patient's blood stream.

The arrangement of the present invention for venting the transducer diaphragm 48 to atmosphere provides a convenient method for calibrating the transducer without these problems. As schematically shown in FIG. 1, a calibration system consisting of a syringe 72 can be easily connected through a T-fitting 70 by way of a small length of tubing 66 to the hole 77 and channel 64b which is provided in the socket 62. The other end of the T-fitting 70 is connected through another length of tubing 66 to a manonometer 68. Stopcock 32 is vented to atmosphere and stopcock 21 is shut off to the transducer. Then, as the plunger 74 of the syringe 72 is withdrawn, air will be evacuated from cavity 41 by means of the space 71 and channels 64a and 64b provided through the plug 60 and corresponding socket 62. It should be noted that socket 62 is provided with a small O-ring type seal 87 (see FIG. 4) which seals the interface between channels 64a and 64b so that the vacuum is maintained. In this manner, a vacuum can be imposed within the cavity 41 so as to deflect the transducer diaphragm 48 thereby generating the calibration pressure needed to calibrate the monitor 28 to the transducer diaphragm 48.

The absolute value of the pressure reading at monitor 28 should be the same as the vacuum reading on manometer 68 so that if there is a difference the monitor 28 can be adjusted until the two readings are the same. Thus, in this manner, the pressure monitoring system can be quickly and easily checked for calibration. Once calibration has been checked, the tubing 66 and calibration system are removed so that channels 64a and 64b are vented to the atmosphere, and stopcock 32 is closed and stopcock 21 is opened to the patient.

It should be appreciated that the manometer 68 and syringe 72 could be replaced by any apparatus for introducing the vacuum used to check the monitor/transducer calibration. For example, a pneumatic transducer tester such as the Model DPM-1 manufactured by Bio-Tek Instruments, Inc., could also be adapted for use in checking the calibration of the monitor 28 and transducer 24. Any means of imposing a known pressure differential across the transducer diaphragm 48 by means of the vent channels 64a and 64b and vent space 71 could be used.

The arrangement described above for checking calibration could be advantageously adapted for use with any transducer. For example, a disposable pressure transducer as described in my copending U.S. application Ser. No. 608,761 could be used with the above-described calibration arrangement, as could other more conventional nondisposable transducers.

Significantly, it should be noted that the calibration equipment connected through tubing 66 is connected at a point within the pressure monitoring system which is completely isolated from the patient tubing 20. In other words, the cavity 41 which is placed in communication with the vacuum created by syringe 72 is completely isolated by means of the partition 43 and dielectric gel 52, as well as by means of the two diaphragms 40 and 38 from coming in contact with the infusion fluid which fills the patient line 20. Accordingly, there is no risk of contamination of the patient nor is there any risk of introducing air into the patient line 20 when checking calibration. This greatly enhances the safety and convenience when it is necessary to calibrate the monitor and transducer.

In order to avoid pressure input from the patient during calibration, stopcock 21 is temporarily closed. However, a further advantage of the apparatus of the present invention is that if stopcock 21 is inadvertently left open, the patient's safety will not be jeopardized as would be the case if calibration were being accomplished using the prior art type sphygmomanometer technique. In the prior art type technique, if the patient line 20 is left open during calibration additional fluid may be infused into the patient whereas such is not the case using the apparatus and method of the present invention.

Figure 4A:
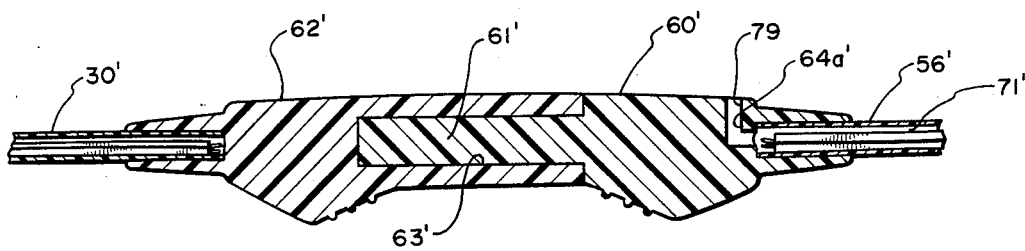
FIG. 4A is a longitudinal sectional view of another embodiment of a plug and socket that may be used in accordance with the apparatus and method of the present invention.

FIG. 4A shows another embodiment of a plug and socket arrangement that can be used in accordance with the apparatus and method of the present invention. In FIG. 4A the plug 60' and soacket 62' are essentially identical in their shape and configuration with the plug 60 and socket 62 as described above in connection with FIGS. 3 and 4, except for the arrangement of the channel 64a' through which the space 71' of cable 56' is vented. As shown in FIG. 4A, in this embodiment socket 62' does not contain any vent channel and the vent channel 64a' of plug 60' is L-shaped and terminates at a small opening 79 provided in the upper surface of plug 60'.

The operation of this plug and socket arrangement is essentially like that described above in connection with FIG. 4. The transducer diaphragm 48 is vented through the small opening 59 (see FIG. 2) in cap 55 and then through the cavity 41 through space 71' and channel 64a'. A calibration system consisting of any suitable equipment for introducing a vacuum through the channel 64a' and space 71' to cavity 41 can be used to impose the pressure differential on the transducer diaphragm 48 for purposes of checking calibration. The calibration equipment is then removed and stopcock 32 is closed and stopcock 21 is opened to the patient so that the transducer diaphragm 48 is vented to atmosphere through channel 64a'.

The plug and socket arrangement of FIG. 4A has the advantage that it may simplify the process used to mold plug 60' and socket 62' since that tolerance required in order to provide an adequate seal at the interface between channels 64a and 64b as in the case of the embodiment of FIG. 4 is eliminated.

Figure 6:
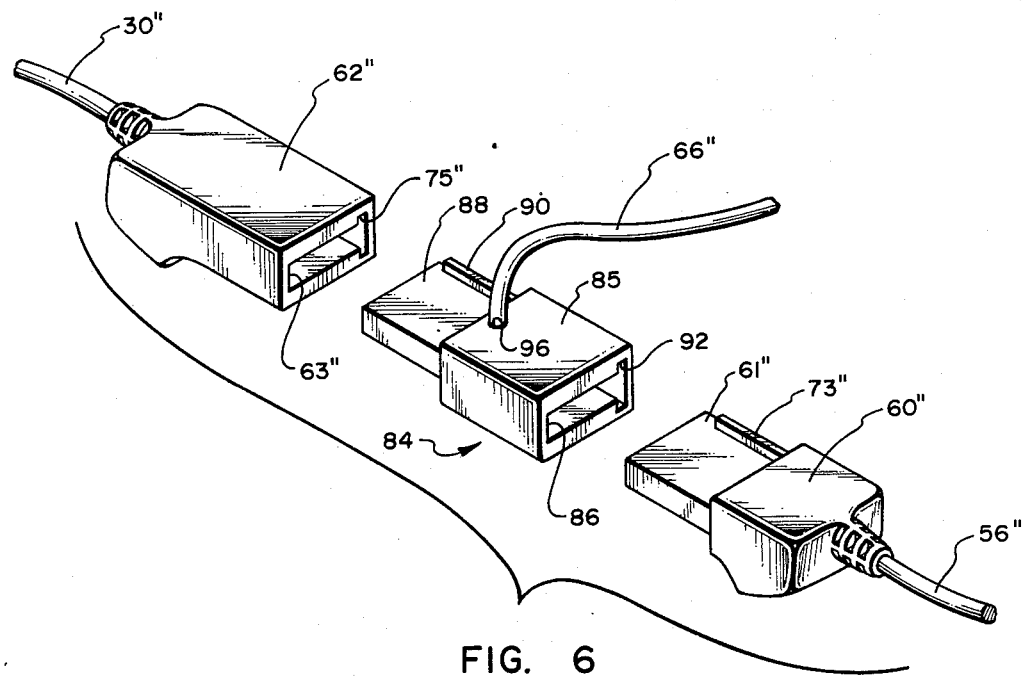
FIG. 6 illustrates a perspective view of a third embodiment of the electrical plug and socket used for interconnecting a monitor to the transducer apparatus, and wherein an intermediate connector is used between the plug and socket.
Figure 7:
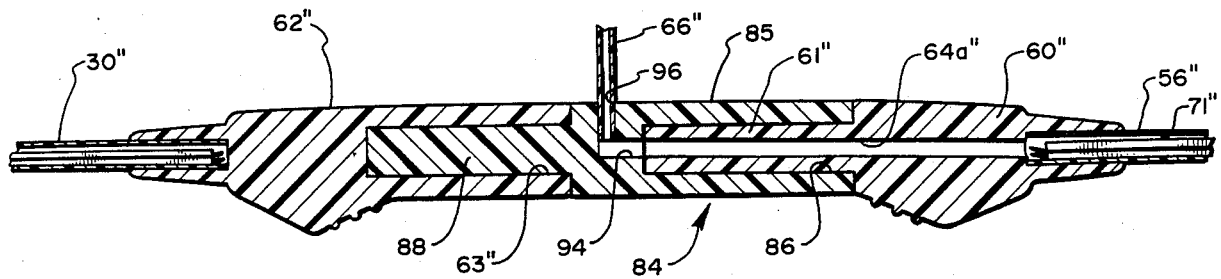
FIG. 7 is a longitudinal sectional view of the plug and socket of FIG. 6 connected to the intermediate connector.
Figure 8:
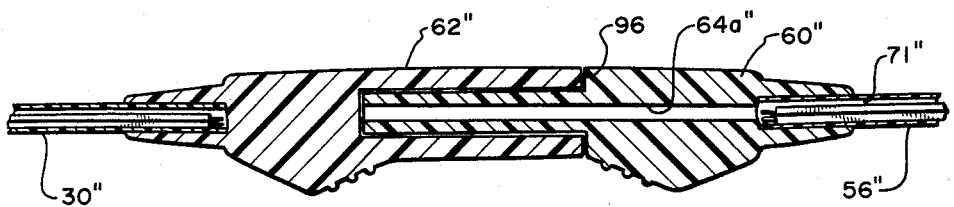
FIG. 8 is a longitudinal sectional view of the plug and socket of FIG. 6 showing the intermediate connector removed from between the plug and socket.

Still another embodiment of a plug and socket arrangement that can be used is illustrated in FIGS. 6–8. In the embodiment of FIGS. 6–8, an intermediate connector generally designated at 84 is used to interconnect plug 60″ with socket 62″. The intermediate connector 84 has one end 85 which is provided with an opening 86 and keyway 92 which receive in mating relationship the male fitting 61' corresponding key 73″. The other end 88 of intermediate connector 84 is configured as a male fitting having a key 90 which is adapted for insertion into the opening 63″ and keyway 75″ of socket 62″.

As illustrated in FIG. 7, intermediate connector 84 has a vent channel 94 which interfaces with the vent channel 64a″ of plug 60″. The channel 94 in turn terminates at a small opening 96 which is adapted to receive the tubing 66″ used in connection with the calibration equipment for imposing a vacuum through vent channel 94 and channel 64a″ back to the cavity 41 (see FIG. 2) which contains the transducer diaphragm 48. Accordingly, the manner of checking calibration using the embodiment of FIGS. 6–8 is the same as previously described in connection with the other two embodiments of FIGS. 4 and 4A.

In the embodiment of FIGS. 6–8, intermediate connector 84 may be a specially machined part having a very close tolerance such that when the intermediate connector 84 is inserted between the plug 60″ and socket 62″ as shown in FIG. 7, the entire plug and socket arrangement is completely sealed except for the vent channels 64a″ and 94 through which the vacuum is introduced. Once calibration has been accomplished, intermediate connector 84 can then be removed as illustrated in FIG. 8. The tolerance between the male fitting 61″ and the opening 63″ of socket 62″ is such that a small space 96 will exist when the intermediate connector 84 has been removed so that the transducer diaphragm 48 will be vented to atmosphere through the channel 64a″ and space 96 when the intermediate connector 84 is removed. This arrangement has the additional advantage that since the intermediate connector 84 is removed during normal transducer operation, there is less risk of plugging the vent and hampering the normal transducer operation.

Figure 5:
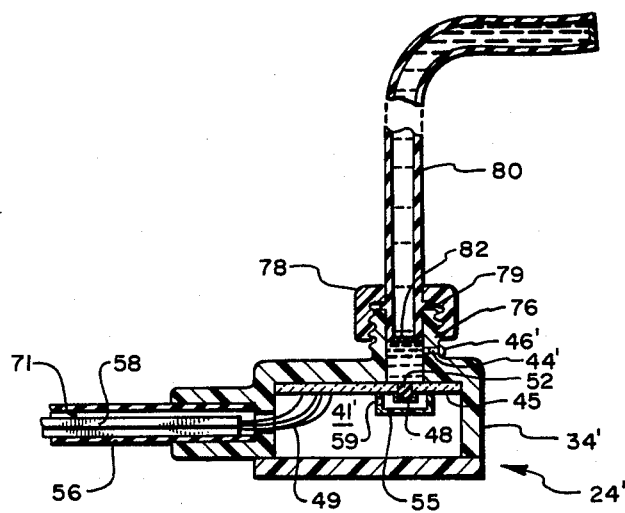
FIG. 5 illustrates in cross-section an alternative embodiment of the pressure transducer apparatus.

FIG. 5 represents an alternative embodiment of the transducer apparatus of the present invention. In FIG. 5, the primary difference of this embodiment with respect to the embodiment previously illustrated and described in connection with FIG. 2 is that the housing 34' has been modified. In FIG. 5, housing 34' forms a single cavity 41' in which the dielectric substrate 45 and electronic components mounted on substrate 45 are contained. As in the prior embodiment, the transducer diaphragm 48 is provided with a fluid coupling comprised of silicon gel 52 which interfaces the transducer diaphragm 48 through a hole formed in the substrate 45. Positioned over the silicon gel 52 is threaded inlet port 76. The threaded inlet port 76 is adapted to receive the end of a tube 80 which provides a fluid-filled coupling in patient line 20 through T-fitting 22 (see FIG. 1) and stopcock 21. The tube 80 is removably attached to the transducer apparatus 24' by means of a cap 78 mounted on the end of tubing 80 and which is adapted to be screwed onto the threaded inlet port 76. A small ridge 79 is formed on the outer surface to retain cap 78 and to permit tubing 80 to be securely anchored to port 76.

The end of tube 80 which is inserted into port 76 is provided with a small diaphragm 82 positioned in the leading end of tube 80. Thus, when tube 80 is attached to the transducer apparatus 24', the transducer apparatus is completely isolated from the infusion fluid by means of the diaphragm 82. Silicon oil may be used to partially fill the inlet port through a small hole 44' which is plugged with a cap 46' similar to the embodiment of FIG. 2. Thus, it will be appreciated that as in the case of the embodiment of FIG. 2, transducer diaphragm 48 is coupled by silicon gel 52 to the silicon oil inside port 76, to diaphragm 82. Transducer diaphragm 48 is also completely isolated from the infusion fluid of patient line 20 by means of diaphragm 82. Thus, the tube 80 replaces the disposable dome 36 and is the portion which is discarded after use.

The transducer diaphragm 48 is vented through hole 59 and cavity 41' in the same manner as the embodiment of FIG. 2 and thus can be safely and conveniently used whenever calibration is necessary.

From the foregoing it will be appreciated that the apparatus and method of the present invention entirely avoids the serious risks and disadvantages inherent in conventional use of a sphygmomanometer to calibrate a transducer. By introducing the calibration pressure on the monitor side of the transducer diaphragm (e.g., the side vented to atmospheric pressure) at a point that is completely isolated from the patient line, the risk of contamination or introduction of air into the patient line is eliminated.

Accordingly, use of the methods and apparatus of the present invention is both safe and convenient. Even if the calibration technician forgets to close the stopcock between the patient and the transducer, no harm will come to the patient. Further, since there is no possibility of introducing air bubbles into the indwelling catheter or patient line, one of the more common sources of inaccurate pressure readings is entirely eliminated.

The present invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. In a direct blood pressure monitoring system including an indwelling catheter and pressure tubing filled with a fluid for communicating blood pressue pulses to a diaphragm of a pressure transducer, and a monitor for displaying data corresponding to said blood pressure pulses, an apparatus comprising means for placing one side of said diaphragm in communication with said blood pressure pulses in said pressure tubing and catheter, means for venting the other side of said diaphragm to atmospheric pressure, and means for introducing a calibration pressure on the side of said diaphragm that is vented.

2. An apparatus as defined in claim 1 wherein said transducer comprises a silicon chip, and wherein said means for placing said one side of said diaphragm in communication with said pressure pulses comprises a housing, said housing having a cavity formed therein in which said transducer is contained and a chamber for receiving a liquid through which said pressure pulses are transmitted.

3. An apparatus as defined in claim 2 wherein said housing further comprises a partition dividing the interior of said housing into an upper chamber for receiving said liquid, and wherein said cavity is formed beneath said partition, and wherein said apparatus further comprises a disposable dome removably attached over said upper chamber.

4. An apparatus as defined in claim 3 wherein said dome comprises a chamber for receiving said fluid used to fill said pressure tubing and catheter, and a dome diaphragm sealing said chamber.

5. An apparatus as defined in claim 3 wherein said housing further comprises a flexible diaphragm sealing said upper chamber.

6. An apparatus as defined in claim 4 wherein said housing further comprises a flexible diaphragm placed in contact with said dome diaphragm such that deflection of said dome diaphragm will be transmitted to said flexible diaphragm of said housing.

7. An apparatus as defined in claim 3 wherein said housing further comprises a hole formed through a side of said housing for introducing said first liquid into said upper chamber, and means for capping said hole.

8. An apparatus as defined in claim 3 further comprising a dielectric substrate secured within said cavity adjacent said partition, said substrate and said partition each comprising a hole formed therethrough in alignment with one another, and a dielectric substance disposed within said holes for transmitting said blood pressure pulses therethrough, and wherein said transducer is mounted on said substrate such that said one side of said transducer diaphragm is in contact with said dielectric substance.

9. An apparatus as defined in claim 2 wherein said housing further comprises a port for receiving a tube, a portion of said port forming an upper chamber for receiving said liquid, and wherein said cavity is formed beneath said port, and wherein said apparatus further comprises a disposable tube removably attached to said port.

10. An apparatus as defined in claim 9 wherein said disposable tube is filled with said fluid used to fill said catheter and pressure tubing, and wherein a leading end of said tube is sealed with a flexible diaphragm and is positioned within said port such that the leading end is adapted to be in contact with said liquid, and wherein a trailing end of said tube is connected to said pressure tubing.

11. An apparatus as defined in claim 9 wherein said housing further comprises a hole formed through a side of said housing for introducing said liquid into said portion of said port which forms said upper chamber, and means for capping said hole.

12. An apparatus as defined in claim 9 further comprising a dielectric substrate secured within said cavity, said substrate comprising a hole formed therethrough and positioned underneath said upper chamber, and a dielectric substance disposed within said hole for transmitting said blood pressure pulses therethrough, and wherein said transducer is mounted on said substrate such that said one side of said transducer diaphragm is in contact with said dielectric substance.

13. An apparatus as defined in claim 2 further comprising a first cable having a plurality of wires electrically connected to said transducer.

14. An apparatus as defined in claim 13 wherein said means for venting said other side of said diaphragm to atmospheric pressure comprises a vent space formed through said first cable in communication with said cavity which contains said transducer.

15. An apparatus as defined in claim 14 further comprising an opaque cap positioned over said transducer.

16. An apparatus as defined in claim 15 wherein said means for venting said other side of said diaphragm to atmospheric pressure further comprises a vent hole formed through a side of said cap.

17. An apparatus as defined in claims 14 or 16 further comprising a plug connected to said first cable and a socket connected to a second cable coupled to said monitor, and wherein said plug comprises a channel formed therethrough in communication with said vent space of said first cable.

18. An apparatus as defined in claim 17 further comprising a channel formed through said socket such that said channels of said plug and socket are in alignment with one another when said plug is joined to said socket, and said channel of said socket terminating at one end in a hole formed in a side of said socket.

19. An apparatus as defined in claim 17 wherein said channel of said plug terminates at one end in a hole formed in a side of said plug.

20. An apparatus as defined in claim 17 further comprising an intermediate connector having one end thereof adapted to receive said plug, and another end thereof adapted for insertion into said socket, and said connector having a channel formed therethrough such that said channels of said plug and said connector are in communication with one another when said plug is joined to said connector, and said channel of said connector terminating at one end in a hole formed in a side of said connector.

21. An apparatus as defined in claim 1 wherein said means for introducing said calibration pressure comprises means for imposing a vacuum on the side of diaphragm that is vented.

22. An apparatus for use in a direct pressure monitoring system in which a catheter is adapted to be inserted into a patient and is connected to pressure tubing filled with a sterile liquid, said apparatus comprising:
a semiconductor pressure transducer element comprising a pressure diaphragm adapted to be deflected by blood pressure pulses communicated through said sterile liquid and further comprising means for transforming said deflections of said diaphragm into corresponding electrical signals;
a housing comprising a chamber filled with a fluid for transmitting said blood pressure pulses through said chamber, and a cavity disposed adjacent to said chamber, said cavity containing said transducer element; and
means removably connected to said chamber of said housing for isolating said chamber from the sterile liquid used to fill said pressure tubing and catheter, such that said apparatus is adapted for re-use by removing and discarding said means.

23. An apparatus as defined in claim 22 wherein said means comprises a disposable dome, said dome comprising a chamber for receiving said sterile liquid and a diaphragm for sealing said chamber of said dome, said diaphragm of said dome being sufficiently flexible to transmit said blood pressure pulses from said sterile liquid to said fluid in said housing chamber.

24. An apparatus as defined in claim 23 wherein said housing further comprises a diaphragm for sealing said housing chamber, said diaphragm of said dome and said diaphragm for sealing said housing chamber being contiguous with one another.

25. An apparatus as defined in claim 22 wherein said housing further comprises a partition dividing the interior of said housing into an upper chamber and a lower cavity disposed beneath said upper chamber, said upper chamber containing said fluid and said lower cavity containing said transducer element.

26. An apparatus as defined in claim 25 further comprising a dielectric substrate mounted in said lower cavity adjacent said partition, and wherein said transducer element is mounted on said substrate.

27. An apparatus as defined in claim 26 wherein said substrate and said partition each have a hole formed therethrough in alignment with one another, each said hole being filled with a dielectric substance and said pressure diaphragm of said transducer element being mounted over said hole of said substrate so as to be in contact with said dielectric substance.

28. An apparatus as defined in claim 26 further comprising an opaque cap mounted to said substrate over said transducer element.

29. An apparatus as defined in claim 22 further comprising an electrical cable containing a plurality of wires electrically connected to said transducer element, and wherein said housing comprises a port through which said wires are introduced into said cavity.

30. An apparatus as defined in claim 22 wherein said isolating means comprises a disposable tube removably connected at a leading end thereof to said chamber of said housing, and connected at a trailing end thereof to said chamber of said housing, and connected at a trailing end thereof to said pressure tubing, and said tube comprising a diaphragm sealing the leading end of said tube so as to isolate said housing chamber from said sterile liquid used to fill said pressure tubing and catheter.

31. An apparatus as defined in claim 30 wherein said housing comprises a threaded inlet port and wherein a portion of said inlet port forms said chamber of said housing, and wherein said leading end of said disposable tube is inserted into the remaining portion of said port and secured by a threaded fitting screwed onto said port.

32. An apparatus as defined in claim 30 further comprising a dielectric substrate mounted in said cavity, and wherein said transducer element is mounted on said substrate.

33. An apparatus as defined in claim 32 wherein said substrate comprises a hole formed therethrough, and further comprising a dielectric substance filled in said hole and in fluid communication with the fluid in said housing chamber, and said diaphragm of said transducer element being mounted to said substrate over said hole and in contact with said dielectric substance.

34. An apparatus as defined in claim 32 further comprising an opaque cap mounted to said substrate over said transducer element.

35. An apparatus as defined in claim 22 further comprising means for venting said cavity to atmospheric pressure, and means for introducing a calibration pressure into said cavity.

36. An apparatus as defined in claim 35 further comprising:
   a first cable having a plurality of wires, said first cable being connected at one end to said housing and comprising a vent space in communication with said cavity, and said first cable being connected at the other end to a plug; and
   a second cable connected to a monitor at one end thereof and connected at the other end to a socket, said socket being removably connected to said plug, and said plug comprising a channel formed therethrough communicating with the vent space of said first cable.

37. An apparatus as defined in claim 36 further comprising a channel formed through said socket such that said channels of said plug and socket are in alignment with one another when said plug is joined to said socket, and said channel of said socket terminating at one end in a hole formed in a side of said socket.

38. An apparatus as defined in claim 36 wherein said channel of said plug terminates at one end in a hole formed in a side of said plug.

39. An apparatus as defined in claim 36 further comprising an intermediate connector having one end thereof adapted to receive said plug, and the other end thereof adapted for insertion into said socket, and said connector having a channel formed therethrough such that said channels of said plug and said connector are in communication with one another when said plug is joined to said connector, and said channel of said connector terminating at one end in a hole formed in a side of said connector.

40. An apparatus as defined in claim 36 wherein said means for introducing said calibration pressure comprises means for imposing a vacuum through said channel of said socket.

41. An apparatus for use in a direct blood pressure monitoring system which includes a catheter adapted to be inserted into a patient and connected to liquid-filled tubing for communicating blood pressure pulses through said liquid-filled catheter and tubing to a diaphragm of a pressure transducer, and a monitor for displaying data corresponding to said blood pressure pulses, said apparatus comprising:
   a housing comprising a chamber filled with a fluid for transmitting said blood pressure pulses through said chamber, and a cavity disposed adjacent to said chamber, said cavity containing said pressure transducer;
   means removably connected to said chamber of said housing for isolating said chamber from said liquid used to fill said pressure tubing and catheter, such that said pressure transducer is adapted for re-use by removing and discarding said isolating means;
   means for placing one side of said diaphragm in fluid communication with said blood pressure pulses transmitted through said liquid-filled pressure tubing and catheter;
   means for venting the other side of said diaphragm through said cavity to atmospheric pressure; and
   means for introducing a calibration pressure into said cavity on the side of said diaphragm that is vented to said atmospheric pressure.

42. In a direct blood pressure monitoring system including an indwelling catheter and pressure tubing filled with a fluid for communicating blood pressure pulses to a diaphragm of a pressure transducer, and a monitor for displaying data corresponding to said blood pressure pulses, a method of calibrating said monitor to said diaphragm of said pressure transducer comprising the steps of:
   placing one side of said diaphragm in communication with said blood pressure pulses in said pressure tubing and catheter;
   venting the other side of said diaphragm to atmospheric pressure; and
   introducing a calibration pressure on the side of said diaphragm that is vented.

* * * * *

UNITED STATES PATENT AND TRADEMARK OFFICE
CERTIFICATE OF CORRECTION

PATENT NO. : 4,610,256

DATED : September 9, 1986

INVENTOR(S) : William D. Wallace

It is certified that error appears in the above-identified patent and that said Letters Patent is hereby corrected as shown below:

Col. 2, line 31, "vessle" should be --vessel--

Col. 10, line 57, "manonometer" should be --manometer--

Col. 11, lines 4-5, "manonometer" should be --manometer--

Col. 11, line 61, "soacket" should be --socket--

Col. 14, line 3, "pressue" should be --pressure--

Signed and Sealed this

Twenty-third Day of August, 1988

Attest:

DONALD J. QUIGG

Attesting Officer   Commissioner of Patents and Trademarks

REEXAMINATION CERTIFICATE (874th)
United States Patent [19]

Wallace

[11] B1 4,610,256
[45] Certificate Issued  Jun. 21, 1988

[54] PRESSURE TRANSDUCER

[75] Inventor: William D. Wallace, Salt Lake City, Utah

[73] Assignee: Medicor, Inc., Salt Lake City, Utah

Reexamination Request:
  No. 90/001,191, Mar. 20, 1987

Reexamination Certificate for:
  Patent No.: 4,610,256
  Issued: Sep. 9, 1986
  Appl. No.: 654,373
  Filed: Sep. 25, 1984

[51] Int. Cl.⁴ .................................................. A61B 5/02
[52] U.S. Cl. ..................................... 128/675; 128/673; 73/706;721;740;4 R
[58] Field of Search ............... 128/672, 673, 675, 748; 73/715, 721, 706, 708, 740, 4 R

[56]         References Cited
              PUBLICATIONS

R. H. S. Murray and N. A. Howe, "A Calibration System for Catheter Transducer Pressure Measurement", *Biomedical Engineering*, May, 1976, pp. 180-182.

Primary Examiner—Edward M. Coven

[57]            ABSTRACT

A pressure transducer which includes a novel apparatus and method for calibrating a pressure transducer to a monitor used in connection with an indwelling catheter to monitor a patient's blood pressure. The pressure transducer includes a transducer diaphragm disposed within a housing cavity. A manometer and a syringe are connected so as to be in communication with the transducer cavity. By partially withdrawing the plunger of the syringe, the pressure in the transducer cavity is reduced, thereby establishing a pressure drop equal to that measured by the manometer across the transducer diaphragm, thus facilitating calibration of the pressure measurement system. Inasmuch as the indwelling catheter is isolated from the pressure calibration apparatus, the methods and apparatus of the present invention avoid any risk of introducing air bubbles or microorganisms into the indwelling catheter.

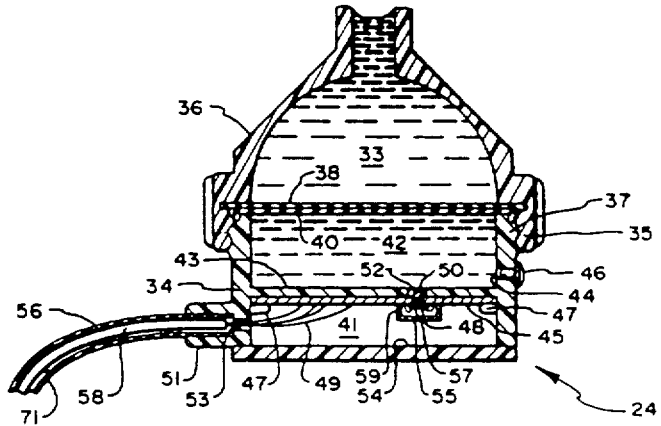

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 22–41 is confirmed.

Claims 1, 13 and 42 are determined to be patentable as amended.

Claims 2–12 and 14–21, dependent on an amended claim, are determined to be patentable.

New claims 43 and 44 are added and determined to be patentable.

1. In a direct blood pressure monitoring system including an indwelling catheter and pressure tubing filled with a fluid for communicating blood pressure pulses to a diaphragm of a pressure transducer, and a monitor for displaying data corresponding to said blood pressure pulses, an apparatus comprising means for placing one side of said diaphragm in communication with said blood pressure pulses in said pressure tubing and catheter, means for venting the other side of said diaphragm to atmospheric pressure, and [means] *a first cable comprising means for electrically connecting said transducer diaphragm to said monitor and said first cable further comprising means* for introducing a calibration pressure on the side of said diaphragm that is vented.

13. An apparatus as defined in claim 2 [further comprising a] *wherein said* first cable [having] *comprises* a plurality of wires electrically connected to said transducer.

42. In a direct blood pressure monitoring system including an indwelling catheter and pressure tubing filled with a fluid for communicating blood pressure pulses to a diaphragm of a pressure transducer, and a monitor for displaying data corresponding to said blood pressure pulses, a method of calibrating said monitor to said diaphragm of said pressure transducer comprising the steps of:

placing one side of said diaphragm in communication with said blood pressure pulses in said pressure tubing and catheter;

venting the other side of said diaphragm to atmospheric pressure; and introducing *by means of a cable used to electrically connect said diaphragm to said monitor* a calibration pressure on the side of said diaphragm that is vented.

*43. In a direct blood pressure monitoring system including an indwelling catheter and pressure tubing filled with a fluid for communicating blood pressure pulses to a diaphragm of a pressure transducer, and a monitor for displaying data corresponding to said blood pressure pulses, an apparatus comprising:*

*a housing comprising a cavity formed therein in which said diaphragm is contained and further comprising a chamber for receiving a liquid through which said pressure pulses are transmitted to one side of said diaphragm;*

*means for venting the other side of said diaphragm to atmospheric pressure; and*

*means for introducing a calibration pressure on the side of said diaphragm that is vented.*

*44. In a direct blood pressure monitoring system including an indwelling catheter and pressure tubing filled with a fluid for communicating blood pressure pulses to a diaphragm of a pressure transducer, and a monitor for displaying data corresponding to said blood pressure pulses, an apparatus comprising:*

*means for placing one side of said diaphragm in communication with said blood pressure pulses in said pressure tubing and catheter; and*

*a cable means for electrically connecting said diaphragm to said monitor and for venting the other side of said diaphragm to atmospheric pressure, and means for sealing said cable means from said atmospheric pressure except at a single location such that a calibration pressure may be selectively introduced through said venting means at said location and such that when not calibrating said diaphragm said other side of said diaphragm will be vented to atmospheric pressure through said single location.*

* * * * *